US009217704B2

(12) United States Patent
Richardson et al.

(10) Patent No.: US 9,217,704 B2
(45) Date of Patent: Dec. 22, 2015

(54) DEVICE AND A METHOD FOR CHARACTERISING A CHROMATIC PROPERTY OF FOODSTUFF

(71) Applicant: Adelaide Research & Innovation Pty Ltd, Adelaide (AU)

(72) Inventors: Andrew Callum Richardson, Kent Town (AU); Sean Manning, O'Halloran Hill (AU); Kristopher John Rowland, Glenalta (AU)

(73) Assignee: SensAbility Pty Ltd, Adelaide (AU)

( * ) Notice: Subject to any disclaimer, the term of this patent is extended or adjusted under 35 U.S.C. 154(b) by 0 days.

(21) Appl. No.: 14/416,335

(22) PCT Filed: Jul. 23, 2013

(86) PCT No.: PCT/AU2013/000809
§ 371 (c)(1),
(2) Date: Jan. 22, 2015

(87) PCT Pub. No.: WO2014/053002
PCT Pub. Date: Apr. 10, 2014

(65) Prior Publication Data
US 2015/0185138 A1    Jul. 2, 2015

(30) Foreign Application Priority Data

Jul. 23, 2012 (AU) .................... 2012903131

(51) Int. Cl.
*G01J 3/46* (2006.01)
*G01N 21/25* (2006.01)
*A47J 37/06* (2006.01)
*A47J 37/08* (2006.01)

(52) U.S. Cl.
CPC .............. *G01N 21/251* (2013.01); *A47J 37/06* (2013.01); *A47J 37/085* (2013.01); *G01N 2201/062* (2013.01)

(58) Field of Classification Search
CPC ................ G01J 3/02; G01J 3/46; G01J 3/50; G01J 3/51; G01J 3/524
USPC ................................... 356/300–445
See application file for complete search history.

(56) References Cited

U.S. PATENT DOCUMENTS 5,004,349 A * 4/1991 Sato et al. .................... 356/402

FOREIGN PATENT DOCUMENTS

GB      2 199 733 A     7/1988
GB      2461080 A      12/2009
(Continued)

OTHER PUBLICATIONS

International Written Opinion issued in PCT/AU2013/000809 mailed Aug. 20, 2013.
(Continued)

*Primary Examiner* — Abdullahi Nur
(74) *Attorney, Agent, or Firm* — RatnerPrestia

(57) ABSTRACT

The present disclosure provides a device for characterizing a chromatic property of foodstuff. The device includes a light source arranged to emit light having at least two wavelengths or wavelength ranges. The light source is further arranged to direct the light to a surface of at least the foodstuff. The device also includes a detector positioned to detect at least a portion of reflected light and arranged to generate an output that is indicative of an intensity of detected reflected light. The device is arranged such that respective outputs are generated for the at least two wavelengths or wavelength ranges. A relation between the output for one of the at least two wavelengths or wavelength ranges and the output for the other or another one of the at least two wavelengths or wavelength ranges is indicative of the chromatic property of the surface of the foodstuff.

20 Claims, 5 Drawing Sheets

(56) References Cited

FOREIGN PATENT DOCUMENTS

| | | |
|---|---|---|
| GB | 2461092 A | 12/2009 |
| JP | 2000-346797 | 12/2000 |

OTHER PUBLICATIONS

International Search Report for PCT/AU2013/000809 mailed Aug. 20, 2013.

IPER issued in PCT/AU2013/000809 dated Feb. 14, 2014.

\* cited by examiner

DEVICE AND A METHOD FOR CHARACTERISING A CHROMATIC PROPERTY OF FOODSTUFF

CROSS REFERENCE TO RELATED APPLICATIONS

This application is the U.S. National Phase Application of PCT/AU2013/000809, filed Jul. 23, 2013 which claims priority to Australian Patent Application No. 2012903131, filed Jul. 23, 2012, the contents of such applications being incorporated by reference herein.

FIELD OF THE INVENTION

The present invention relates to a device a method and an apparatus for characterising a chromatic property of foodstuff, and relates in particular, though not exclusively, to a device and a method for determining a change in colour of breadstuff, such as bread in a toaster.

BACKGROUND OF THE INVENTION

A conventional toaster has a timer used to set the time for toasting one or more slices of bread. However, the optimal toasting time is dependent on a range of factors. For example, the toasting time depends on the colour of the bread (white, grey or brown), the type of the bread (multigrain or rye), sugar content, the moisture content and the state of the bread (frozen, stale, etc.). Further, the toasting time depends on a condition of the bread such as fresh, or frozen. Thus, it is difficult to select the optimal time for toasting and browning the bread.

There is need for improvement.

SUMMARY OF THE INVENTION

In accordance with a first aspect of the present invention, there is provided a device for characterising a chromatic property of foodstuff, the device comprising:
 a light source arranged to emit light having at least two wavelengths or wavelength ranges, the light source further being arranged to direct the light to a surface of at least the foodstuff; and
 a detector positioned to detect at least a portion of reflected light and arranged to generate an output that is indicative of an intensity of detected reflected light;
 wherein the device is arranged to generate respective outputs for the at least two wavelengths or wavelength ranges, and to determine a relation between the output for one of the at least two wavelengths or wavelength ranges and the output for the other or another one of the at least two wavelengths or wavelength ranges as a function of a temperature to correct an influence of the temperature on the detected reflected light, wherein the relation is indicative of the chromatic property of the surface of the foodstuff.

For the ease of understanding, the term "light" is used throughout the patent specification as a synonym for electromagnetic radiation which may include visible light and also invisible light.

The device may comprise a sensor for measuring the temperature.

In one embodiment, the device is arranged to adjust at least one of the generated respective outputs as a function of the measured temperature.

The device may further comprise a controller arranged to control a change in the chromatic property of the foodstuff by controlling a source that is arranged to effect the change in the chromatic property. The source may, for example, comprise a heating element. The controller may be arranged to control a rate of the change in the chromatic property of the surface of the foodstuff. The controller may also be arranged to end or interrupt a change in the chromatic property of the foodstuff. For example, the controller may be arranged to disable the source that is arranged to effect the change of the chromatic property.

In one embodiment, the light source comprises at least two component light sources that are arranged to emit light having the respective wavelengths or wavelength ranges. For example, the light source may comprise at least two light emitting diodes ("LEDs") that emit light having the respective wavelengths or wavelength ranges. The light source may be arranged such that the foodstuff is illuminated with light generated by a first component light source and light generated by a second component light source in sequence. Alternatively, the at least two component light sources may be arranged to illuminate the foodstuff simultaneously. The detector may comprise at least one respective detector element for each component light source.

In an alternative embodiment, the light source is a broadband light source, such as a single broadband light source that is arranged to emit the light having the at least two wavelengths or wavelength ranges.

The device typically is arranged such that a diameter of a surface area of the foodstuff that is exposed to the light and/or a detection area is at least 0.5 cm, 1 cm, 2.5 cm, 5 cm or 10 cm (Full width at half maximum intensity).

The device may comprise at least one filter that is arranged to filter the light such that the detector detects light having the respective wavelength ranges or wavelengths in sequence. In one specific example, the device comprises at least two filters that are arranged to filter the light to provide light having the respective wavelength or wavelength ranges.

The device may further comprise an optical splitter for splitting the light emitted from the broadband light source into at least two light beams. In this case, the device typically is arranged such that the at least two light beams have the respective wavelengths of wavelength ranges.

The detector may for example comprise an optical spectrum analyser or a photo-detector that is arranged to determine light intensities associated with the at least two wavelength ranges or wavelengths simultaneously or sequentially. The detector may for example be a semiconductor detector comprising silicon, InGaAs or any other suitable semiconductor. The detector may also be any other light sensitive component such as a light dependent resistor.

The first wavelength or wavelength range may be selected in a manner such that the intensity of light reflected from the foodstuff and having the first wavelength or wavelength range is dependent on the chromatic property. For example, the first wavelength range may include the range of 450 nm-500 nm, 500 nm-550 nm, 550 nm-600 nm, 650 nm-700 nm, 750 nm-800 nm or even higher and the first wavelength may be a wavelength within any one of these ranges. In a specific example, the wavelength range may be selected based on the full-width at half maximum of the light intensity emitted by the light source.

The second wavelength or wavelength range typically is selected such that the intensity of the reflected portion of light having the second wavelength or wavelength range is less dependent on the chromatic property than the reflected light having the first wavelength or wavelength range. In one specific example, the reflected intensity of light having the second wavelength or wavelength range is largely independent from a change in the chromatic property.

The second wavelength range may be within any suitable wavelength range including for example the visible, near infrared or infrared range. For example, the second wavelength range may include the range of 800 nm-1800 nm, 800 nm-1400 nm, 850 nm-1150 nm, or 850 nm-950 nm and the second wavelength may be a wavelength within any one of these ranges. For example, the second wavelength range may be within approximately 750 nm to 1400 nm.

In one embodiment, the device further comprises a determiner arranged to determine the relation between the output for one of the at least two wavelengths or wavelength ranges and the output for the other or another one of the at least two wavelengths or wavelength ranges. For example, the relation may be a ratio, a difference, a combination of the aforementioned or any other suitable relation such as a polynomial, logarithmic or exponential relation. Specifically, the relation may be a difference of the respective outputs over a sum of the respective outputs. This particular relation may be referred to as normalised difference.

Further, the determiner may be arranged to determine a change in a value associated with the output for the one of the at least two wavelengths or wavelength ranges relative to the output for the other or another of the at least two wavelengths or wavelength ranges. In one specific example, the determiner is arranged to determine a change in detected light having the first wavelength or wavelength range relative to detected light having the second wavelength range or wavelength.

The determiner may be arranged to determine the relation periodically or continuously and typically is coupled to, or forms a part of, the controller. Further, the determiner may be arranged to determine whether the determined relation exceeds or falls below a predetermined threshold, such as a predetermined difference, a predetermined ratio or a predetermined normalised difference.

The detector may further be arranged to detect a background light when the light source does not emit the light having the at least two wavelengths or wavelength ranges, and to generate an output indicative of the intensity of the background light. The background light may for example be ambient light from a heating element, ambient room light, or light from any other source. In one embodiment, the determiner may further be arranged to correct the respective outputs and/or the determined relation using the generated output indicative of the intensity of the background light.

In one embodiment, the detector is positioned to detect reflected light exclusively from the surface of the foodstuff. The detector typically comprises a single detector element, but may alternatively also comprise more than one detector element, such as two detector elements that are arranged to detect portions of reflected light from the surface of the foodstuff. For example, the detector may comprise a detector element for each light source component.

The device may be arranged to illuminate one or more areas of the surface of the foodstuff.

The device may further comprise an element for shielding or transferring heat away from the detector, such as a heat shield or a heat sink.

In one embodiment, the chromatic property is a colour of the foodstuff. For example, the device may be arranged to determine a brownness of breadstuff.

In a further embodiment, the device may be a handheld unit for characterising the chromatic property of the foodstuff.

In accordance with a second aspect of the invention, there is provided a method for characterising a chromatic property of foodstuff, the method comprising the steps of:

providing the foodstuff having a surface;
illuminating the surface of the foodstuff with light having at least two wavelengths or wavelength ranges;
detecting at least a portion of light that is reflected;
obtaining a temperature;
generating respective outputs for the at least two wavelengths or wavelength ranges, an output being indicative of an intensity of the detected reflected light; and
characterising the chromatic property of the surface of the foodstuff by determining a relation between the output for one of the at least two wavelengths or wavelength ranges and the output for the other or another one of the at least two wavelengths or wavelength ranges as a function of the obtained temperature to correct an influence of the temperature on the detected reflected light.

The step of obtaining a temperature may comprise measuring the temperature.

In one embodiment the method comprises a step of adjusting at least one of the generated respective outputs as a function of the measured temperature.

The method may comprise a step of controlling a change in the chromatic property of the surface of the foodstuff by controlling a source that is arranged to effect the change in the chromatic property. The method may further comprise controlling a rate of the change in the chromatic property of the foodstuff and may also comprise controlling a duration of the change in the chromatic property of the foodstuff. The step of controlling the change in the chromatic property typically is conducted as a function of the determined relation.

In one specific example, the respective outputs are generated for first and second wavelengths or wavelength ranges. For example, the method may comprise illuminating the surface of the foodstuff with light having the first wavelength or wavelength range, and with light having the second wavelength or wavelength range during effecting the chromatic change. In this case, the method may comprise detecting reflected light including the first wavelength or wavelength range, and reflected light having the second wavelength or wavelength range.

Determining the relation may comprise determining a ratio, a difference, a combination of the aforementioned or any other suitable relation such as a logarithmic or exponential relation. Specifically, the relation may be a difference of the respective outputs over a sum of the respective outputs.

Further, the step of determining the relation may comprise determining a change in value associated with the output for the one of the at least two wavelengths or wavelength ranges relative to the output for the other or another of the at least two wavelengths or wavelength ranges.

The method may further comprise a step of effecting a chromatic change of a surface of the foodstuff. Effecting the chromatic change of a surface of the foodstuff may comprise exposing the surface of the foodstuff to a source for effecting the chromatic change, such as a heating source. The source may, for example, comprise a heating element.

The method may further comprise a step of detecting a background light when the surface of the foodstuff is not illuminated with the light having the at least two wavelengths or wavelength ranges, and a step of generating an output indicative of the intensity of the background light. Additionally, the method may comprise a step of correcting the respective outputs and/or the determined relation using the generated output indicative of the intensity of the background light.

The step of determining the relation may be conducted repeatedly in sequence. Alternatively, the step of determining the relation may be conducted continuously.

In one embodiment, the method is conducted to determine a first relation indicative of the chromatic property of the foodstuff, and thereafter determining a second relation, or a series of relations, indicative of the chromatic property of the foodstuff. For example, the first and second relations may be conducted while a change in the chromatic property of the foodstuff is effected and the method may be conducted to determine that change in the chromatic property.

The method may further comprise a step of measuring a temperature such that an influence of the temperature on the generated outputs can be corrected.

In accordance with a third aspect of the invention, there is provided an apparatus for effecting a chromatic change of foodstuff, the apparatus comprising:

a source arranged to effect chromatic change of a surface of the foodstuff; and the device in accordance with the first aspect of the invention.

The apparatus may be any suitable heating apparatus such as an electric appliance or a gas operated appliance. For example, the apparatus may be a toaster for breadstuff, a solar oven or a roasting appliance for coffee beans.

The source may be a heating source that is arranged to effect a change in the chromatic property. For example, the source may comprise a heating element. Alternatively, the source may for example be provided in the form of an oven cavity.

The apparatus may further comprise a controller arranged to control a change in the chromatic property of the foodstuff by controlling the source that is arranged to effect the chromatic change. The controller may be arranged to control a rate of a change in the chromatic property of the foodstuff. The controller may also be arranged to end or interrupt a change in the chromatic property of the foodstuff. The controller may further be arranged to deactivate the source that is arranged to effect the chromatic change when a predetermined relation threshold has been achieved or exceeded.

In one embodiment, the apparatus comprises an interface for facilitating selection of a predetermined relation by a user. The interface may further be arranged to communicate the determined relation. For example, the determined relation may be communicated directly or indirectly by virtue of an audio signal or a visual signal. Additionally or alternatively, the apparatus may be arranged to transmit the determined relation to a handheld unit for example in a wireless manner.

Additionally or alternatively, the interface is arranged to communicate whether the determined relation exceeds the predetermined threshold, for example, by virtue of an audio signal or a visual signal.

The apparatus may further comprise a sensor for measuring a temperature such that an influence of the temperature on the generated output can be corrected.

In a further embodiment, the apparatus comprises an element for shielding or transferring heat away from the detector. The element may comprise a heat shield or a heat sink.

BRIEF DESCRIPTION OF THE DRAWINGS

The present invention will now be described, by way of example only, with reference to the accompanying drawings, in which.

DESCRIPTION OF AN EMBODIMENT OF THE INVENTION

Figure 1:
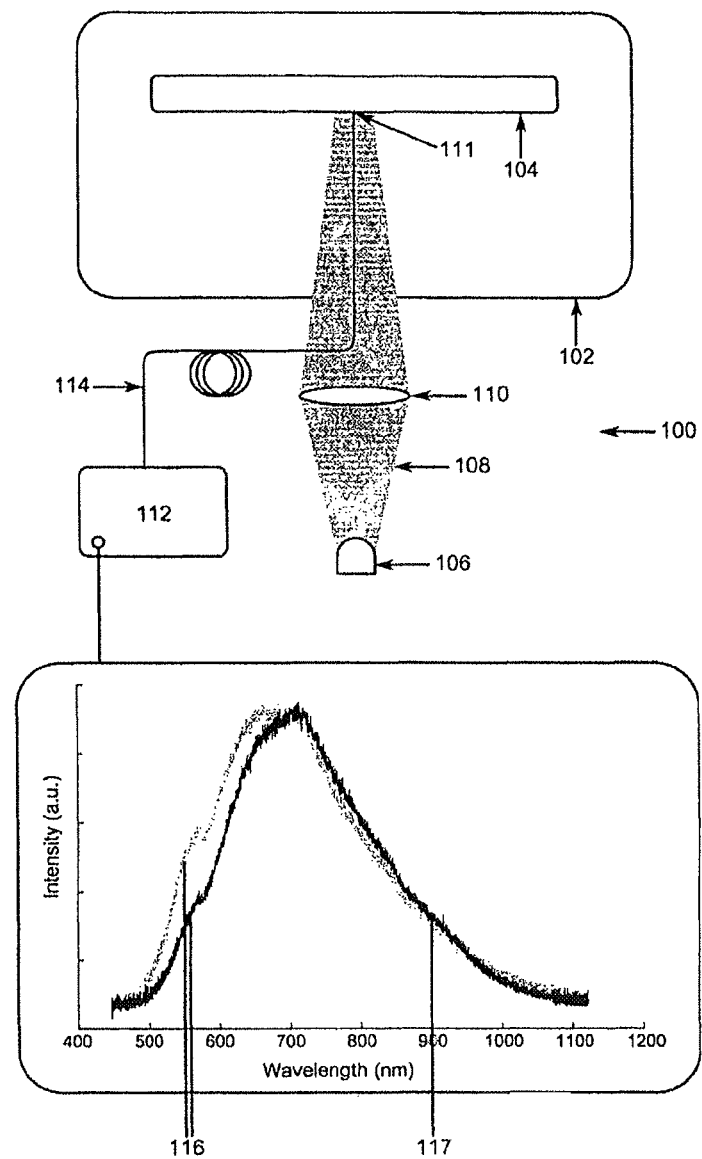
FIG. 1 is a schematic block diagram of components of a device in accordance with an embodiment of the present invention.

Referring initially to FIG. 1, components of the device 100 for characterising a chromatic property of foodstuff are shown. In this particular example, the device 100 is incorporated into a toaster 102 and is arranged to determine brownness of bread 104 that is caused by a heating element (not shown). The browning of the bread in the toaster (or the browning of other foodstuff) is typically caused by processes such as the Maillard reaction or caramelisation.

Figure 2:
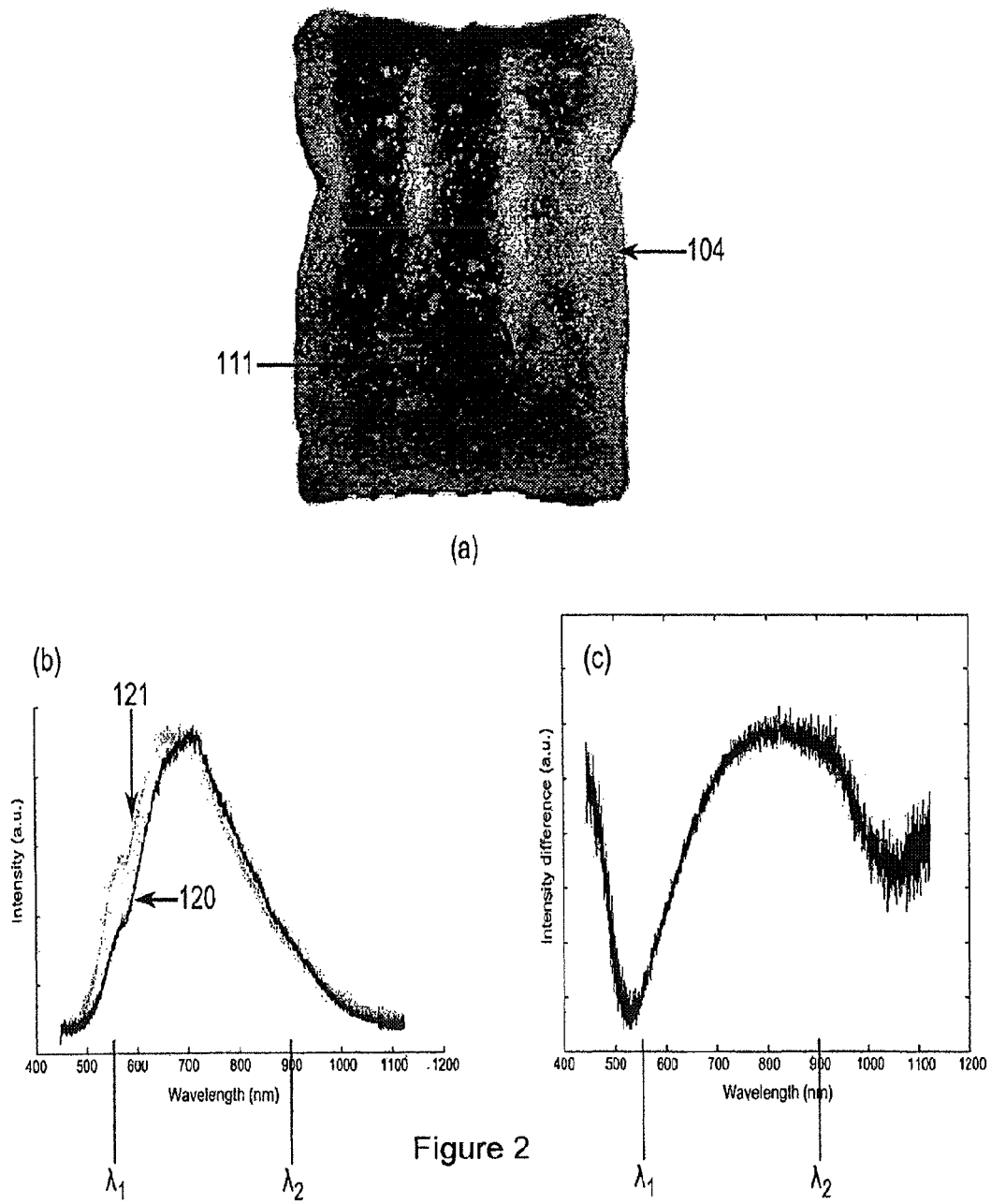
FIGS. 2 and 3 show images of toasted breadstuff and diagrams that are determined in accordance with a method step in accordance with embodiments of the present invention.

The device comprises a broadband light source 106 that emits light having numerous wavelength ranges that together form a continuum. The light source 106 directs light 108 to a surface of the bread 104. In this particular example the light source 106 is a light bulb that emits white light 108. The light 108 is directed through a lens 110 that focuses the light 108 onto an area 111 of the surface of the bread 104. In this example and as further shown in FIGS. 2a) and 3a), the light 108 is directed to a central area 111 of the surface of the bread 104. FIG. 2a) shows an image of a toasted white bread and FIG. 3a) shows an image of toasted multi-grain bread. A person skilled in the art will appreciate that the area 111 may have any suitable size or location on the surface of the bread 104.

The device 100 further comprises a detector 112 for detecting at least a portion of reflected light 114. In this embodiment, the detector 112 is provided in the form of an optical spectrum analyser that detects a portion of the reflected light 114. The portion of reflected light 114 that is detected by the detector 112 is directed to the detector 112 by an optical fibre. Examples of detected spectra of light are shown in FIGS. 2b) and 3b). A person skilled in the art will appreciate that the detector of the device in accordance with embodiments of the invention may comprise one or more detector elements.

Figure 3:
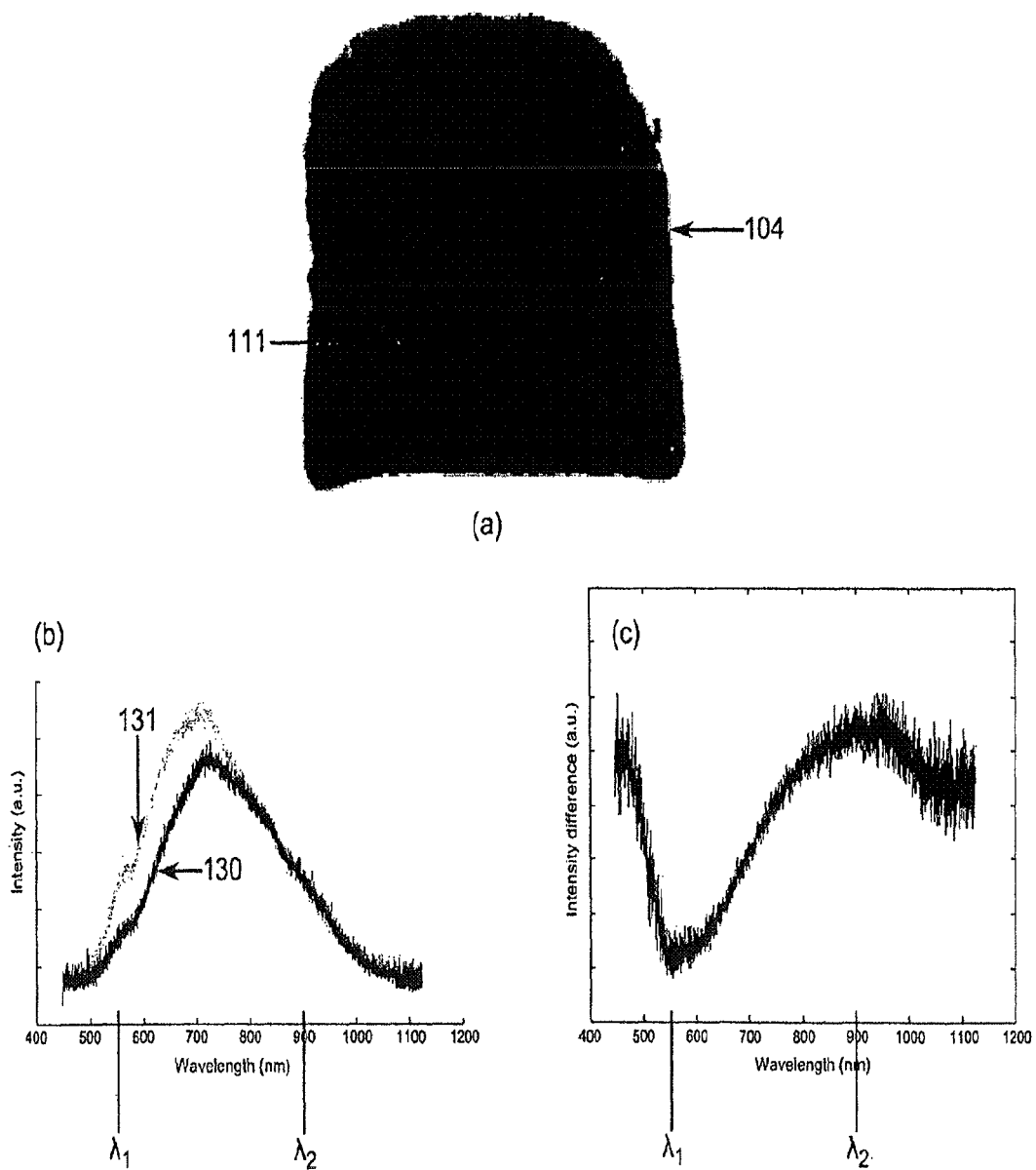

The detector generates respective outputs for two wavelength ranges of the broadband spectrum of light emitted by the light source 106. In this particular embodiment, the respective outputs are combined in one diagram as shown in FIGS. 2b and 3b. A relation between the output for one wavelength range and the output for the other wavelength range is indicative of the brownness of the surface of the bread 104. In this example the detector 112 generates two outputs 116, 117 that are indicative of the detected intensity at respective wavelength ranges. A relation between the two outputs 116, 117 at the selected wavelength ranges is indicative of the brownness of the bread 104.

In this embodiment the first wavelength range is selected such that the intensity of the reflected portion of light 114 associated with the first wavelength range changes as a function of the brownness of the bread 104. In this example the first wavelength range is within 500 nm to 600 nm (such as around 550 nm).

The second wavelength range is selected such that the intensity of the reflected portion of light 114 associated with the second wavelength range does not appreciably change as a function of the brownness of the bread 104, in comparison to the first wavelength range. In this example, the second wavelength range is within 850 nm to 950 nm (such as around 900 nm). The intensity associated with the second wavelength range provides a reference that does not change appreciably as a function of the brownness of the bread 104.

The relation between the two outputs for the respective wavelength ranges is further illustrated in FIGS. 2b) and 3b), and also in FIGS. 2c) and 3b).

FIGS. 2b) and 3b) show the spectra that are generated by the spectrum analyser of the detector 112. Spectra 120 and 130 relate to light that was reflected from the bread 104 before the bread 104 was exposed to the heating element 104. Second spectra 121 and 131 relate to light that was detected after a predetermined toasting time. FIG. 2c) illustrates a calculated ratio between the spectra 120 and 121 and FIG. 3c) illustrates a calculated ratio between the spectra 130 and 131.

It can be seen that for a signal wavelength $\lambda_1$ of approximately 550 nm the output changes as a function of the brownness of the surface of the bread 104. However, for a reference wavelength $\lambda_2$ of approximately 900 nm the corresponding output is substantially constant.

Values that are indicative of the intensities at the wavelengths $\lambda_1$ and $\lambda_2$ are then directed to a determiner (not shown) that is arranged to determine a ratio between the values. In this particular example, the determiner is provided in the form of a processor in a computing system.

By determining the ratio between the values that are indicative of the intensities at the wavelengths $\lambda_1$ and $\lambda_2$ the processor can characterise the brownness of the bread 104. Further, a change in brownness may additionally be determined.

A person skilled in the art will appreciate that other relations between the two values may be determined such as a difference, a ratio, a combination of a ratio and a difference, a polynomial, logarithmic or exponential relation or any other suitable relation.

Figure 4:
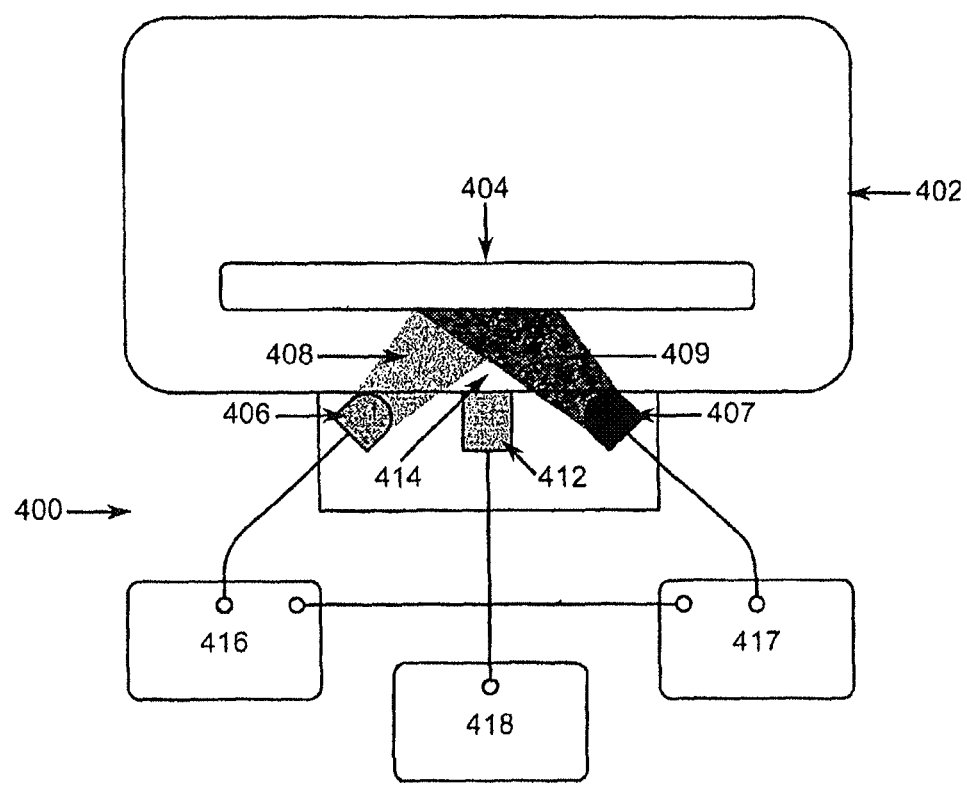
FIG. 4 is a schematic block diagram of components of a device in accordance with a further embodiment of the present invention.

Referring now to FIG. 4, there is shown a device 400 in accordance with a specific embodiment of the invention. The device 400 is incorporated into a toaster 402 and arranged to characterise brownness of bread 404. A person skilled in the art will appreciate that the device may be incorporated in any suitable apparatus that comprises a source for effecting a chromatic change of a surface of the foodstuff. The source may, for example, be a heating source which may comprise a heating element. Alternatively, the device may be provided in the form of a handheld device.

In this particular embodiment, the device 400 comprises two light emitting diodes (LEDs) 406 and 407 that emit light 408, 409 having the respective wavelength ranges. The LEDs 406, 407 are arranged to direct the light 408, 409 to an area on the surface of the bread 404 such that a detector 412 (which includes a photo diode) can detect a reflected portion of the light 414. In this and other examples, the LEDs 406, 407 direct the light 408, 409 to the same area on the surface of the bread 404. The area is sufficiently sized such that local variations of the surface of the bread 404 such as grains, raisins, surface shape, surface defects or the like do not substantially affect the generated outputs. A suitable spot may have a diameter of approximately 2 cm FWHM in intensity. Further, the area that is detected by the detector is substantially identical to the spot that is illuminated by the LEDs.
Full Width In this particular example, the LED 406 emits light 408 at a signal wavelength of 525 nm which corresponds to green light. The LED 407 emits light 409 at a reference wavelength of 940 nm which corresponds to near-infrared light.

The photodiode of the detector 412 generates outputs for the detected reflected light having wavelengths $\lambda_1$ and $\lambda_2$. In this example, the photodiode of the detector 412 has a peak response at 850 nm and has approximately 60% responsiveness at the wavelengths $\lambda_1$ (525 nm) and $\lambda_2$ (940 nm). The output is further transferred to a processor 418 (which may also be provided in the form of a suitable integrated chip) that is arranged to determine a relation between output values associated with the wavelengths $\lambda_1$ and $\lambda_2$. By determining the relation, the brownness of the surface of the bread can be characterised 404.

In this particular example, the detector 412 further detects a background light when the light emitting diodes 406, 407 do not emit any light having the respective wavelength ranges. The photodiode of the detector 412 further generates an output indicative of the intensity of the background light. The background light may for example be ambient light from a heating element, ambient room light, or light from any other sources being reflected from the bread surface, reflected from other parts of the toaster, or directly illuminating the detector 412.

In this example, the LEDs 406, 407 are driven by pulse generators 416, 417 (which may be incorporated on a suitable integrated chip), that are linked together by virtue of a trigger 419. The trigger 419 is arranged such that the two LEDs 406, 407 are operated in an alternating manner and consequently the photodiode of the detector 412 detects reflected light at the wavelengths $\lambda_1$ and $\lambda_2$ in sequence. The pulsing may also be arranged such that there is a period of time where neither of the two LEDs emits light and the detector detects the above-mentioned background light so that the background light can be measured and accounted for.

In this example, the processor 418 determines the relation between values associated with the wavelengths $\lambda_1$ and $\lambda_2$ by determining a difference of the values at the wavelengths $\lambda_1$ and $\lambda_2$ over a sum of the values at the wavelengths $\lambda_1$ and $\lambda_2$. This relation may also be referred to as normalised difference. The normalised difference can be determined using the following equation (1):

$$ND = \frac{(I_2 - I_1)}{(I_1 + I_2)} \qquad \text{equation (1)}$$

where ND is the normalised difference, $I_1$ is the value at the wavelength $\lambda_1$ which is indicative of the intensity of the reflected portion of light and $I_2$ is the value at the wavelength $\lambda_2$ which is indicative of the intensity of the reflected portion of light.

The normalised difference provides a relative change in the relation that is typically less susceptible to fluctuations in the light sources, e.g., the LEDs or ambient light. Such fluctuations may for example be due to voltage fluctuations, drive current fluctuations or other causes such as gradual decrease in light emission as the LED reaches the end of its lifetime.

The processor 418 may correct the determined normalised difference by subtracting the detected background light. This may be done using the following equation (2):

$$ND = \frac{(I_2 - I_1)}{(I_1 + I_2 - 2 \cdot I_0)}$$

where ND is the normalised difference, $I_1$ is the value at the wavelength $\lambda_1$ which is indicative of the intensity of the reflected portion of light, $I_2$ is the value at the wavelength $\lambda_2$ which is indicative of the intensity of the reflected portion of light and $I_0$ is the value indicative of the intensity of the background light.

A person skilled in the art will appreciate that other suitable arrangements of the device 400 are envisaged. For example, the two LEDs 406 and 607 may emit light concurrently onto the surface of the bread 404 and the at least a portion of reflected light 114 may be detected by sequentially filtering the light before it is detected with a single detector 112.

Alternatively, the detector 412 of the device 400 may comprise more than one detector element, e.g., more than one photodiode. For example, the device may comprise a detector element for each light emitting diode. Further, the device may comprise an additional detector element for detecting the background light. In the case of having more than one detector element, the detector elements may be directed in a substantially similar direction to reduce effects of focussing to a point with a variable sample distance.

As illustrated in FIGS. 1 and 4, the devices 100 and 400 may be incorporated into a toaster 102, 402. However, a person skilled in the art will appreciate that other apparatus are envisaged. For example, the apparatus may be an electric or gas-operated appliance. Specifically, the appliance may be arranged to toast breadstuff or to roast coffee beans, or the like.

The toaster 402 comprises a heating element that is arranged to cause brownness on the surface of the bread 404.

In this embodiment, the toaster 402 further comprises a sensor for measuring a temperature (not shown). A change in temperature may affect the output generated by the detector of the device, due to the sensitivity of the detector or LED emission spectra being affected. By measuring the temperature, the generated output and/or the determined relation may be corrected. For example, the sensor may be positioned in the proximity of the detector or the light source such as the LEDs. Correction of the influence of a change in temperature within the toaster 102 may be performed by a number of suitable methods. In one example, the generated outputs are corrected by respective correction factors. A correction factor typically depends on the shape of the response curve of the detector with respect to wavelength. The correction factor may also depend on a change in intensity or wavelength spectrum emitted by the light source with increasing temperature.

In another example, the sensitivity of the detector is corrected electronically as a function of a change in temperature. However, other suitable correction methods are envisaged.

In a further embodiment of the present invention (not shown), the toaster 402 comprises an element for shielding or transferring heat away from the detector of the device. In this way, an effect of a change in temperature within the toaster on the detector of the device may be reduced. The element may comprise a heat shield and/or a heat sink that are located in close proximity of the detector. The heat shield may be attached to a portion of the detector that is facing the heating element such that at least a portion of heat from the heating element can be reflected or absorbed. The heat sink may be arranged such that at least a portion of heat from the heating element is dissipated away from the detector. In a specific example, a metal shield is located between the detector and the heating element, the metal shield further comprises an aperture through which the detector can detect light.

In this particular example, a determiner 418 additionally determines whether the determined relation between the outputs generated for the signal and the reference wavelengths exceeds or falls below a predetermined threshold. The toaster 402 comprises a controller (which may be provided in the form of an integrated chip) arranged to control the toaster 402 as a function of the determined relation. The controller is provided in the form of a processor that deactivates the heating element when the determined relation exceeds the predetermined threshold. Thus, the change in chromatic property of the surface of the bread 404 is stopped. However, a person skilled in the art will appreciate that the controller may also be arranged to control the element that effects the chromatic change of the bread. For example, the controller may be arranged to control a heating rate.

The toaster 402 comprises in this embodiment an interface that facilitates a user to select the predetermined threshold. The interface may be provided in the form of a touch screen that displays a quantity that relates to the determined relation, and may be used to select a threshold darkness at which the toasting process is automatically stopped. However, other suitable forms of the interface are envisaged. For example, when the determined relation exceeds the predetermined threshold, the user may be informed by virtue of an audio signal or a visual signal. Further, wireless data transmission may be established and the wireless data transmission may be used to inform the user or may enable the user to control a function of the device, such as setting the predetermined threshold.

In a further example, the interface may be arranged to provide an output indicative of the chromatic property or a change thereof. The output may be provided by virtue of a visual or audio signal. Additionally or alternatively, the output may be transmitted to a handheld unit. The relation may for example be transmitted by virtue of wi-fi or Bluetooth. A person skilled in the art will appreciate that other wireless or wired transmissions are envisaged.

In addition, for safety purposes the controller automatically deactivates the heating element when the determined relation exceeds a safety threshold, e.g., in order to avoid burning a sample. For additional safety purposes, the controller may be arranged to deactivate the heating element after a maximum period of time.

In an alternative embodiment (not shown), the device comprises filter elements that have transmission windows in the proximity of the wavelengths $\lambda_1$ and $\lambda_2$. The light source may, for example, generate white light that is filtered by the filters and the device may be arranged such that the filtered reflected light is detected by the detector. In this example the light source may comprise two component light sources or the device may comprise an optical splitter that splits the light into two component beams and the light of the component beams is subsequently filtered. The detector may comprise a single (active) detector element and may be arranged to detect the filtered light in sequence. Alternatively, the detector may comprise two or more detector elements and the device may be arranged such that the detector components detect light having respective wavelengths or wavelength ranges substantially simultaneously.

Figure 5:
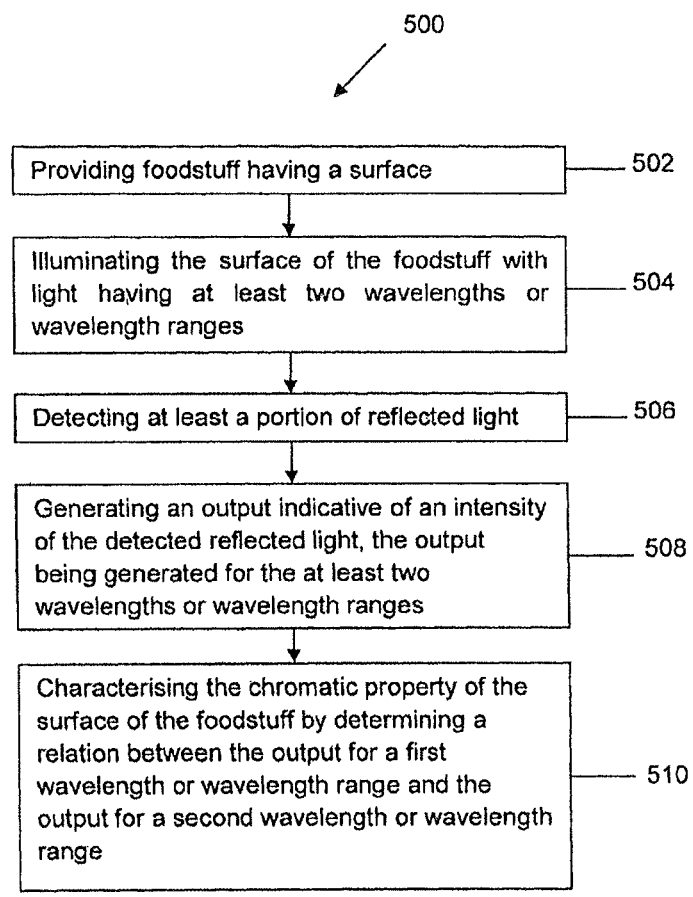
FIG. 5 illustrates a method in accordance with embodiments of the present invention.

Referring now to FIG. 5, a method 500 in accordance with embodiments is illustrated. In a first step 502, a foodstuff is provided having a surface. The surface of the foodstuff is illuminated with suitable light 504. In a further step 506, at least a portion of reflected light is detected. An output is generated 508 that is indicative of an intensity of the detected reflected portion of light. Respective outputs are generated for at least two wavelengths or wavelength ranges. In the next step 510, the chromatic property of the surface of the foodstuff is characterised by determining a relation between the output for a first wavelength or wavelength range and the output for a second wavelength or wavelength range.

Modifications and variations as would be apparent to a skilled addressee are deemed to be within the scope of the present invention. For example, a person skilled in the art will appreciate that the device may comprise any suitable number of light sources that emit two or more wavelengths or wavelength ranges, and/or any suitable number of detectors that are optionally filtered to detect the at least a portion of reflected light. Further, the device 100 may comprise two (or more) detector elements with respective filters. In this case the light source 106 may direct light 108 of a broadband wavelength range onto the surface of the bread 104 and the filters filter the reflected light such that light having the at least two wavelength ranges is detected in sequence. A single detector element of the detector 112 may be arranged to detect the reflected and subsequently filtered light. Alternatively, the apparatus may comprise filters that filter the generated broadband light prior to reflection. Again, a single detector element of the detector 112 may be arranged to detect the at least a portion of the filtered and subsequently reflected light 114.

The invention claimed is:

1. A device for characterising a chromatic property of foodstuff, the device comprising:
    a light source arranged to emit light having at least two wavelengths or wavelength ranges, the light source further being arranged to direct the light to a surface of at least the foodstuff;
    a detector positioned to detect at least a portion of reflected light and arranged to generate an output that is indicative of an intensity of detected reflected light;
    wherein the device is arranged to generate respective outputs for the at least two wavelengths or wavelength ranges, and to determine a relation between the output for one of the at least two wavelengths or wavelength ranges and the output for the other or another one of the at least two wavelengths or wavelength ranges as a function of a temperature to correct an influence of the temperature on the detected reflected light, wherein the relation is indicative of the chromatic property of the surface of the foodstuff.

2. The device of claim 1 comprising a sensor for measuring the temperature.

3. The device of claim 1 wherein the device is arranged to adjust at least one of the generated respective outputs as a function of the temperature.

4. The device of claim 1 further comprising a controller that is arranged to control a change in the chromatic property of the foodstuff by controlling an element that effects the change in the chromatic property.

5. The device of claim 4 wherein the controller is arranged to control a rate of the change in the chromatic property of the foodstuff.

6. The device of claim 5 wherein the controller is arranged to interrupt the change in the chromatic property of the foodstuff.

7. The device of claim 1 wherein the light source comprises at least two component light sources that are arranged to emit light having the respective wavelengths or wavelength ranges, wherein the at least two light components sources are light emitting diodes.

8. The device of claim 7 wherein the detector comprises at least one respective detector element for each component light source.

9. The device of claim 1 wherein the first wavelength or wavelength range is selected in a manner such that an intensity of the light reflected from the foodstuff having the first wavelength or wavelength range is dependent on the chromatic property.

10. The device of claim 1 wherein the second wavelength or wavelength range is selected such that an intensity of the reflected portion of light having the second wavelength or wavelength range is less dependent on a change in chromatic property than an intensity of the reflected portion of light having the first wavelength range.

11. The device of claim 10 wherein the second wavelength or wavelength range is selected such that the intensity of the reflected portion of light having the second wavelength or wavelength range is substantially independent from a change in the chromatic property.

12. The device of claim 1 being arranged to determine a change in the chromatic property by determining a change in determined relations.

13. The device of claim 1 being arranged to determine whether the determined relation or the determined change in the chromatic property exceeds or falls below a predetermined threshold.

14. The device of claim 1 wherein the detector is further arranged to detect a background light when the light source does not emit the light having the at least two wavelengths or wavelength ranges, and to generate an output indicative of the intensity of the background light.

15. An apparatus for effecting a chromatic change of foodstuff, the apparatus comprising:
    a heating source arranged to effect chromatic change of a surface of the foodstuff; and
    the device of claim 1.

16. The apparatus of claim 15 further comprising an interface for facilitating selection of a predetermined relation by a user.

17. The apparatus of claim 15 further comprising an interface for providing an output that is indicative of the relation and/or for exceeding or falling below a predetermined relation.

18. A method for characterising a chromatic property of foodstuff, the method comprising the steps of:
    providing the foodstuff having a surface;
    illuminating the surface of the foodstuff with light having at least two wavelengths or wavelength ranges;
    detecting at least a portion of light that is reflected;
    obtaining a temperature;
    generating respective outputs for the at least two wavelengths or wavelength ranges, an output being indicative of an intensity of the detected reflected light; and
    characterising the chromatic property of the surface of the foodstuff by determining a relation between the output for one of the at least two wavelengths or wavelength ranges and the output for the other or another one of the at least two wavelengths or wavelength ranges as a function of the obtained temperature to correct an influence of the temperature on the detected reflected light.

19. The method of claim 18 comprising a step of adjusting at least one of the generated respective outputs as a function of the measured temperature.

20. The method of claim 18 comprising controlling a change in the chromatic property by controlling an element that effects the change in the chromatic property.

* * * * *